United States Patent
Cockcroft et al.

(10) Patent No.: US 7,951,763 B2
(45) Date of Patent: May 31, 2011

(54) USE OF HIGH SOLIDS SOLUTION OF A CATIONIC COPOLYMER IN PERSONAL CARE FORMULATIONS AND PERSONAL CARE FORMULATIONS OBTAINED THEREFROM

(75) Inventors: Robert Cockcroft, West Yorkshire (GB); Eleanor Bernice Ridley, West Yorkshire (GB); Valerie Reynolds, West Yorkshire (GB)

(73) Assignee: BASF SE, Ludwigshafen (DE)

( * ) Notice: Subject to any disclaimer, the term of this patent is extended or adjusted under 35 U.S.C. 154(b) by 160 days.

(21) Appl. No.: 10/415,405

(22) PCT Filed: Nov. 2, 2001

(86) PCT No.: PCT/EP01/12734
§ 371 (c)(1),
(2), (4) Date: Apr. 29, 2003

(87) PCT Pub. No.: WO02/40622
PCT Pub. Date: May 23, 2002

(65) Prior Publication Data
US 2004/0029768 A1    Feb. 12, 2004

(30) Foreign Application Priority Data
Nov. 16, 2000 (GB) .................................. 0027978.6

(51) Int. Cl.
*C11D 3/37* (2006.01)
*A61K 8/42* (2006.01)
*A61K 8/72* (2006.01)

(52) U.S. Cl. ........ 510/123; 510/159; 510/384; 510/391; 510/475; 510/501; 510/504; 424/401; 424/70.15; 424/70.16; 424/70.17

(58) Field of Classification Search .................. 510/123, 510/159, 384, 391, 475, 501, 504; 424/401, 424/70.15, 70.16, 70.17
See application file for complete search history.

(56) References Cited

U.S. PATENT DOCUMENTS

| | | | |
|---|---|---|---|
| 3,986,825 A * | 10/1976 | Sokol | 8/406 |
| 4,675,178 A * | 6/1987 | Klein et al. | 424/65 |
| 4,865,838 A * | 9/1989 | Gross et al. | 424/47 |
| 4,867,966 A | 9/1989 | Grollier et al. | 424/71 |
| 5,037,632 A | 8/1991 | Gross et al. | 424/47 |

(Continued)

FOREIGN PATENT DOCUMENTS

BM    98/22088    5/1998

(Continued)

OTHER PUBLICATIONS

NALCO, Product Bulletin, MERQUAT®, Polyquaternium 7 Series, Water Soluble Polymers for Personal Care, 3 pages, (2003).

(Continued)

*Primary Examiner* — Brian P Mruk
(74) *Attorney, Agent, or Firm* — Shiela A. Loggins

(57) ABSTRACT

Use of an aqueous solution of a cationic copolymer in a personal care composition, characterized in that the cationic copolymer is formed from a cationic monomer and a nonionic monomer, wherein said cationic copolymer has an average molecular weight in the range 30,000 to 300,000 and the aqueous solution has a concentration of 20 to 50% by weight and a viscosity of less than 10,000 cP at 25° C. The invention also comprises cosmetic compositions obtained from the aqueous solution of the cationic copolymer.

8 Claims, 2 Drawing Sheets

U.S. PATENT DOCUMENTS

| | | | | |
|---|---|---|---|---|
| 5,242,684 A | | 9/1993 | Merianos | 424/78.07 |
| 5,338,541 A | * | 8/1994 | Matz et al. | 424/70.16 |
| 5,558,859 A | | 9/1996 | Cretois | 424/70.15 |
| 6,028,041 A | | 2/2000 | Decoster et al. | 510/119 |

FOREIGN PATENT DOCUMENTS

| | | |
|---|---|---|
| DE | 3401037 | 7/1985 |
| EP | 0331930 | 9/1989 |
| WO | 97/26860 | 7/1997 |
| WO | WO 98/22088 * | 5/1998 |
| WO | 99/20243 | 4/1999 |

OTHER PUBLICATIONS

English language abstract for JP 10007536 printed from esp@cenet.com (Nov. 25, 2005).

English language abstract for JP 5310541 printed from esp@cenet.com (Nov. 25, 2005).

* cited by examiner

USE OF HIGH SOLIDS SOLUTION OF A CATIONIC COPOLYMER IN PERSONAL CARE FORMULATIONS AND PERSONAL CARE FORMULATIONS OBTAINED THEREFROM

The present invention relates to an aqueous solution of a high solids cationic copolymer wherein the solution has a relatively low viscosity & the methods for using such polymers in personal care applications.

It is known that cationic polymers are used as conditioning agents in cosmetic formulations for keratin-containing substrates, such as those currently used in hair & skin products. Such cationic polymers display the ability to be adsorbed onto keratin surfaces & to resist removal by water rinse-off. This property is referred to as substantivity. An effective cationic conditioner should maintain a high substantivity to the keratin surface.

Such conditioning formulations commonly contain one or more anionic surfactant(s) and/or amphoteric surfactant(s) and/or nonionic surfactant(s) to provide cleaning properties for the keratin surface. Ideally, the cationic conditioner should be compatible with the surfactants used to give a more commercially desirable, clear formulation. Incompatibility presents itself as haze or precipitation which is commercially undesirable.

WO-A-9726860 describes the use of Polyquaternium-7® in a personal care formulation. Polyquaternium-7® is a 50/50 wt/wt copolymer of diallyl dimethyl ammonium chloride with acrylamide having a molecular weight of about 1 million. Typically such polymers are prepared and used as low concentration aqueous solutions.

However, a particular problem with prior art formulations, for instance those containing Polyquaternium-7® is that it is difficult to achieve the right combination of rheology and viscosity. In particular it is difficult to achieve the right rheology and viscosity whilst maintaining or improving substantivity to hair/skin, damage due to combing and/or scale lifting.

It is an object of the present invention to provide a cationic polymeric ingredient for use in a personal care composition which provides improved rheology, viscosity and maintains or improves substantivity to hair/skin and/or scale lifting and/or improved resistance to combing. It is a further objective to provide a hair care composition which has improved pouring characteristics and improves upon the substantivity to hair and improves scale lifting.

Surprisingly we have found a copolymer which performs effectively as a conditioning agent for keratin-containing substrates with the advantage of being a low viscosity, high active solids solution, thus enabling ease of handling (such as pouring and pumping)& use (such as mixing into shampoo formulations). The process used results in a copolymer having a low residual monomer content.

This invention concerns an aqueous solution of a cationic copolymer with molecular weight in the range 30,000 to 300,000, having a concentration of between 20-50% by weight active polymer, wherein the solution has a viscosity of less than 10,000 cP (mPa·s) at 25° Celsius. In particular the invention relates the use of said aqueous solution in preparing a cosmetic formulation. The viscosity is measured using RVT Brookfield viscometer using spindle 3 at 10 rpm.

The molecular weight is determined by gel permeation chromatography (GPC). Typically the GPC method may be ideally be determined by employing the following features.

| | |
|---|---|
| columns: | TSK PWXL G6000 + G3000 + guard |
| mobile phase: | pH 4.7 acetate buffer |
| flow rate: | 0.5 ml/min |
| polymer standards: | polyethylene oxide & polyethylene glycol |
| sample size: | 100 microlitres |

In this method the columns are connected in series in a column oven set at 40° C. A pump is used to deliver the mobile phase from a solvent reservoir at a nominal flow rate of 0.5 ml/min. A differential refractive index detector (DRI) is connected in series after the columns and connected to a Personal Computer via a data capture unit. The columns are calibrated with a range of polyethylene oxide and polyethylene glycol standards. Each standard is analysed and a calibration curve constructed of retention versus the logarithm of the peak molecular weight using a third order polynomial fit. The polymer is desirably diluted in mobile phase to give an approximate concentration of 0.15% and analysed using the described method.

The aqueous solution preferably has a concentration of 30 to 45% by dry weight.

The aqueous solution preferably has a viscosity of from 1000 to 10,000 cP at 25° Celsius, measured by Brookfield RVT viscometer.

The solution preferably comprises a copolymer comprising from 25 to 90% by weight of nonionic monomer units and from 10 to 75% by weight of cationic monomer units.

A preferred solution comprises a copolymer from 70 to 80% by weight of nonionic monomer units and 20 to 30% by weight of cationic monomer units.

The nonionic monomer may be any nonionic monomer with preferred monomers selected from the group:

unsaturated N-substituted amides, e.g. N-vinyl formamide, N-vinyl caprolactam, N-vinyl pyrolidone (meth)acrylates having mono- or multi hydroxy functional group(s) e.g. Hydroxyl ethyl acrylate (HEA), hydroxylethyl methacrylate (HEMA), hydroxy propyl acrylate (HPA), hydroxylpropyl methacrylate (HPMA), glycerol mono-acrylate, trimethylolpropane monoacrylate acrylamide and its derivatives, e.g. N-hydroxymethylacrylamide, N-tris(hydroxymethyl)methylacrylamide, other N-alkyl or N-alkoxy substituted acrylamides, e.g. N,N-dimethyl acrylamide and acrylamide derivatives.

A preferred nonionic monomer is acrylamide or a derivative thereof.

The cationic monomer may be any cationic monomer. Preferred cationic monomers may be selected from the group consisting:

dialkyl amino alkyl(meth)acrylamide and preferably, acrylate, as acid addition or, preferably, quaternary ammonium salts, and diallyl dialkyl ammonium halides.

Preferred acrylates and methacrylates are di-$C_{1-4}$ amino ethyl(meth)acrylates and preferred acrylamides and (meth)acrylamides are di-$C_{1-4}$ alkyl amino alkyl(meth)acrylamides, in particular dimethyl amino ethyl(meth)acrylate (DMAE(M)A) and dimethyl amino propyl(meth)acrylamides (DMAP(M)A) with the respective methacrylate and methacrylamide compounds being particularly preferred, as acid addition and, preferably quaternary ammonium salts.

A particular preferred cationic monomer is diallyl dimethyl ammonium chloride (DADMAC).

The copolymer preferably has a molecular weight from 30,000 to 300,000, more preferably 40,000 to 250,000. An especially preferred molecular weight is about 150,000.

The aqueous solution may have a pH of any value, however a preferred pH range is from pH 3 to pH 7.5. Most preferred pH values are from pH 4.5 to pH 6.5.

The cationic content of the copolymer, based on 100% active polymer, may range from 0.6 to 4.5 moles/kg.

The aqueous solution may comprise some unreacted monomer resulting from the copolymerisation of nonionic & cationic monomers, for example less than 20 ppm.

The aqueous solution may comprise a preservative, such as those commonly used in cosmetics, drugs and foods. Such preservatives include phenoxy ethanol, benzoic acid, esters of p-hydroxybenzoic acid, DMDM hydantoin, imidazolidinyl urea, diazodinyl urea, methylchloroisothiazolinone, methylisothiazolinone. Preferred preservatives include phenoxy ethanol and p-hydroxybenzoic acid propyl ester and salts thereof and p-hydroxybenzoic acid methyl ester and salts thereof.

The aqueous solutions of the present invention are preferably compatible with anionic, amphoteric or nonionic surfactants which are included in personal care formulations for the purpose of cleansing the skin or hair and as emulsifiers in cosmetics. Anionic surfactants commonly used in such formulations include but are not limited to the sodium, ammonium, triethanolamine, magnesium or other common salts of alkyl sulfates, ethoxylated alkyl sulfates, derivatives of sarcosine, taurine, isethionic acid, sulfosuccinic acid or ethoxylated/propoxylated versions of these. Amphoteric surfactants commonly used in such formulations include but are not limited to the quaternized alkyl or substituted alkyl derivatives of N,N-dimethyl glycine, amino propane sulfonic acids or salts thereof, alkyl-substituted amino acids (Including salts and alkyl-substituted imino acids). Nonionic surfactants commonly used in such formulations include but are not limited to amine oxides, condensation products of fatty alcohols with glucose and ethoxylated/propoxylated fatty alcohols or mixtures thereof.

The addition of cationic polymers to personal care formulations containing anionic surfactants such as shampoos or other cleansing formulations results in the formation of a highly surface active association complex. However, careful control of the ratio of anionic surfactant: cationic polymer contained in such formulations is critical to maintain clarity. The preferred method to evaluate the compatibility of a cationic polymer in an anionic surfactant system uses a triangular phase diagram and is adapted from "Anionic and Cationic Compounds in Mixed Systems" by J. Caelles, Asociación de Investigación de Detergentes (A.I.D); F. Comelles, J Sánchez Leal, J. L. Parra and S. Anguera, Instituto de Tecnologica Quimica y Textil (C.S.I.C), Barcelona, Spain, published in Cosmetics and Toiletries Vol. 106, April 1991. Solutions of the preferred anionic surfactant, Sodium Laureth Sulfate, and the preferred composition of cationic polymer are prepared at equal concentrations of active material and mixed at various dilutions in deionised water.

Another aspect of the invention is a method of producing an aqueous solution of a cationic copolymer with molecular weight in the range 30,000 to 300,000 having a concentration of 20 to 50% by weight and a viscosity of less than 10,000 cP at 25° Celsius by continuous addition polymerisation. Processes are already known by which the aqueous solution of the present invention may be produced, including adiabatic polymerisations.

The continuous addition polymerisation process involves an aqueous reaction medium, preferably deionised water, which may contain a chelating agent, preferably EDTA sodium salt, and an organic acid, preferably hydrated citric acid. This reaction medium is heated to reflux and a suitable polymerisation initiator, such as ammonium persulphate, dissolved in water is added.

Then a mixture of the nonionic and cationic monomers in water are added at a feed rate of 0.5 to 30 hours, preferably 1 to 5 hours. The nonionic and cationic monomers may be added separately to the reaction mixture at different feed rates, i.e. one monomer feed rate may be faster than the other. Initiator dissolved in water is also added at a feed rate of from 0.5 to 30 hours, preferably 1 to 5 hours. After addition of all the monomer and initiator mixtures, the reaction mixture is then refluxed for a period of from 0.1 to 5 hours, preferably 0.5 to 1.5 hours. The pH of the reaction mixture may then be adjusted to a pH of any value, preferably in the range of from pH 3 to pH 6. A suitable base may be used for this pH adjustment, such as dilute sodium hydroxide solution. The reaction mixture may then be warmed to a temperature of from 40° C. to 90° C., preferably 65° C. to 70° C.

To reduce the amount of residual monomer, a solution of sodium metabisulphite in water may be added to the reaction mixture after polymerisation is complete. The reaction mixture may then be warmed to a temperature of from 40° C. to 90° C., preferably 65 to 70° C., for a period of from 0.1 to 5 hours, preferably 0.5 to 1.5 hours. At this point any suitable preservatives may be added to the solution.

A further aspect of this invention is the use of an aqueous solution of a cationic copolymer with molecular weight in the range 30,000 to 300,000 having a concentration of 20 to 50% by weight and a viscosity of less than 10,000 cP at 25° Celsius in a cosmetic formulation.

Such cosmetic formulations can be in a number of physical forms, such as liquid, gel, cream, lotion, emulsion, and will typically include water and/or cosmetically acceptable solvents such as lower alcohols, polyalcohols or glycol ethers.

Such formulations include but are not limited to hair preparations such as conditioners and shampoos, skin cleansers, moisturisers, body wash formulations such as shower gels and other detergent formulations used for personal hygiene.

Additionally the preferred composition can be used in emulsion based formulations including but not limited to skin creams, hand and nail creams, facial moisturisers, sun protection creams, artificial tanning aids, depilatories, hair conditioners, and temporary and permanent hair colours. A preferred application is a conditioning shampoo for washing the hair combined with providing conditioning properties to the keratin fibres.

The cosmetic composition may contain from 0.01% to 4% by weight based on the total weight of the cosmetic formulation of the aqueous solution of the present invention, preferably from 0.01 to 2%. Preferred compositions can also contain electrolytes, cosmetically acceptable preservative systems, cosmetically acceptable colours, fragrances, sequestering agents, thickeners, emollients, sun filters, silicones, softening agents.

The following examples further illustrate the present invention:

EXAMPLE 1

Preparation of Aqueous Copolymer

Deionised water (185.3 g) was charged to the reactor and stirring commenced, EDTA sodium salt (0.1 g) and citric acid monohydrate (4.0 g) dissolved in deionised water (10.0 g) were charged to the reactor. The contents of the reactor were then heated to reflux.

Diallyl dimethyl ammonium chloride monomer (166.7 g @ 60%) and acrylamide monomer (600 g @ 50%) were charged to the feed vessel.

Ammonium persulphate (7.52 g) and deionised water (30 g) were mixed to dissolve and charged to the initiator feed vessel.

Immediately before starting the monomer and initiator feeds a charge of ammonium persulphate (0.48 g) dissolved in deionised water (1.92 g) was added to the reactor.

The monomer feed was added at a rate of 3 hours. The initiator feed was added at a rate of 3.5 hours. On completion of feeds the reactor was maintained at reflux for a further 1 hour then cooled. The pH was adjusted to approximately pH 4.5 by the addition of sodium hydroxide solution (46%) and then the reactor was warmed up to 65 to 70° C.

Sodium metabisulphite (2.0 g) was dissolved in deionised water (8.0 g) and charged to the vessel. The reactor was maintained at 65 to 70° C. for 1 hour with stirring before being cooled.

Para-hydroxybenzoic acid propyl ester sodium salt (0.2 g) and para-hydroxybenzoic acid methyl ester sodium salt (1 g) were dissolved in deionised water (20 g) and then charged to the vessel and stirred. Final adjustments to pH and solids were then made as required prior to run off. The resulting polymer was a 75:25 Acrylamide:DADMAC copolymer supplied at 40% solids, with a weight average molecular weight of about 100,000 as determined by Gel Permeation Chromatography.

FORMULATION EXAMPLE 2

Conditioning Hair Shampoo

| Ingredient | % w/w |
| --- | --- |
| Water | to 100 |
| Sodium Laureth Sulfate | 30.00 |
| Cocamidopropyl Betaine | 10.00 |
| PEG-7 Glyceryl Cocoate | 2.00 |
| 75:25 Acrylamide: DADMAC copolymer at 40% solids | 2.00 |
| DMDM Hydantoin | 0.15 |
| Disodium Salt Benzenesulfonic Acid, 2,5-Dichloro-4-[4,5-Dihydro-3-Methyl-5-Oxo-4-[(Sulfophenyl)Azo]-1H-Pyrazol-1-yl]- | 0.0002 |
| 2,2'-[(9,10-Dihydro-9,10-Dioxo-1,4-Anthracenediyl)Diimino]Bis(5-Methyl)Benzenesulfonic Acid, Disodium Salt | 0.0001 |
| Citric Acid | to pH 6.5 |
| Perfume | 0.02 |
| Sodium Chloride | qs |

Method of Manufacture:

Water is weighed into an appropriate vessel and colours added. 75:25 Acrylamide: DADMAC copolymer at 40% solids prepared according to Example 1 is added with moderate stirring followed by the rest of the ingredients in order.

FORMULATION EXAMPLE 3

Everyday Conditioning Shampoo

| Ingredient (INCl Name) | % w/w |
| --- | --- |
| Water | to 100 |
| Ammonium Lauryl Sulfate | 20.00 |
| Ammonium Laureth Sulfate | 10.00 |
| 75:25 Acrylamide: DADMAC copolymer at 40% solids | 1.50 |
| DMDM Hydantoin (and) Iodopropynyl Butylcarbamate | 0.15 |
| 4,5-Dihydro-5-Oxo-1-(4-Sulfophenyl)-4-[(4-Sulfophenyl)Azo]-1H-Pyrazole-3-Carboxylic Acid, Trisodium Salt | 0.0002 |
| Citric Acid | to pH 6.5 |
| Perfume | 0.02 |
| Sodium Chloride | qs |

Method of Manufacture:

Water is weighed into an appropriate vessel and colour added. 75:25 Acrylamide: DADMAC copolymer at 40% solids prepared according to Example 1 is added with moderate stirring followed by the rest of the ingredients in order.

FORMULATION EXAMPLE 4

Mild Conditioning Shampoo

| Ingredient (INCl Name) | % w/w |
| --- | --- |
| Water | to 100 |
| Coco-Glucoside | 37.50 |
| Ammonium Lauryl Sulfate | 15.00 |
| 75:25 Acrylamide: DADMAC copolymer at 40% solids | 2.00 |
| Glycerin | 2.00 |
| Imidazolidinyl Urea | 0.15 |
| Disodium 2,5-Dichloro-4-[4,5-Dihydro-3-Methyl-5-Oxo-4-[(4-Sulfophenyl)AZO]-1H-Pyrazol-1-yl]Benzenesulfonate | 0.0002 |
| Citric Acid | to pH 6.5 |
| Perfume | 0.02 |

Method of Manufacture:

Water is weighed into an appropriate vessel and colour added. 75:25 Acrylamide: DADMAC copolymer at 40% solids prepared according to example 1 is added with moderate stirring followed by the rest of the ingredients in order.

FORMULATION EXAMPLE 5

Skin Cream

| Ingredient | % w/w |
| --- | --- |
| Water | to 100 |
| 75:25 Acrylamide: DADMAC copolymer at 40% solids (Prepared according to Example 1) | 4.00 |
| Glycerin | 2.00 |

-continued

| Ingredient | % w/w |
|---|---|
| Dimethicone | 2.00 |
| Paraffinum Liquidum | 3.00 |
| Sodium Acrylates Copolymer (and) Paraffinum Liquidum (and) PPG-1 Trideceth-6 | 2.50 |
| Phenoxyethanol (and) Methylparaben (and) Ethylparaben (and) Butylparaben (and) Propylparaben (and) Isobutylparaben | 0.25 |
| Perfume | 0.02 |

Method of Manufacture:

All ingredients are mixed in a suitable vessel apart from the thickening agent, which is added with rapid stirring.

EXAMPLE 6

The following tests compare the use of the cationic polymer composition in cosmetic compositions according to the present invention with commercially available polymer composition Polyquaternium-7®.

In the following discussion FIG. 1 is a diagram of a Zeiss UMSP-80 microspectrophometer.

SUBSTANTIVITY TO HAIR

Substantivity to hair is a measure of the amount of polymer deposited on the hair and is linked to the feel and condition of the hair swatch. The adsorption of cationic polymers onto bleached and reduced human hair fibres can be monitored by microfluorometry using fluorescent labels.

The surface of bleached and reduced hair is strongly anionic because of the formation of cysteic acid groups. These groups form the adsorption sites for the tagged cationic conditioner. The instruments used for quantitative determination of fluorescence on the fibre surface are microspectrophotometers equipped for incident light illumination. The test was carried out using a Zeiss UMSP-80 microspectrophometer for incident illumination and fluorescence intensity measurements.

Figure 1:
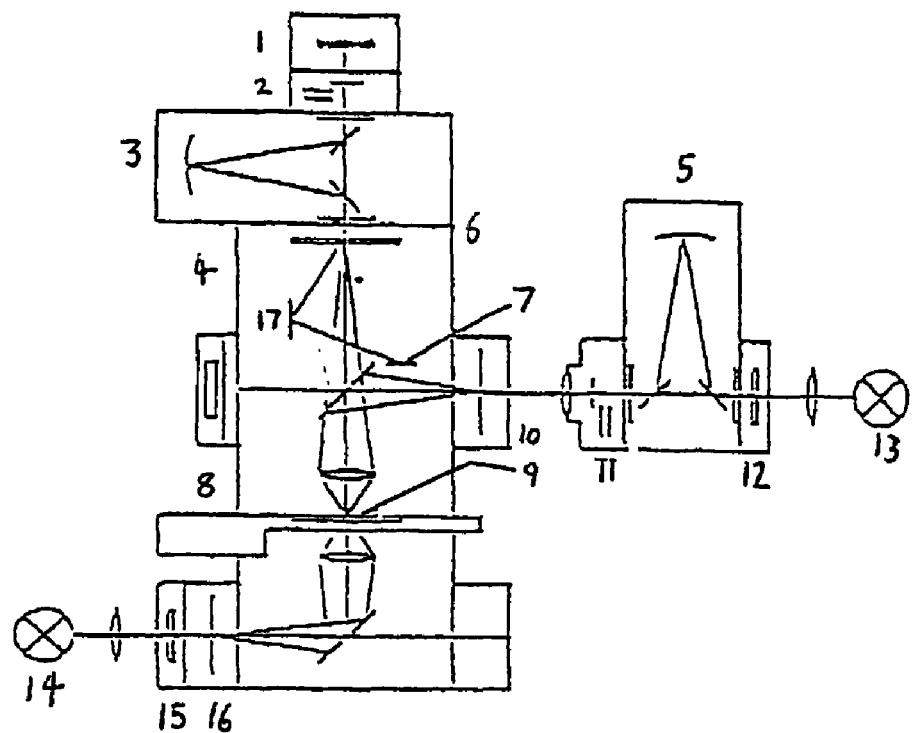

A diagram of this equipment is shown in FIG. 1. In FIG. 1 the following key applies:
1 PMT—Detector
2 Filter 2
3 VIS—Monochromator 2 (360-850 nm)
4 Photometer Head
5 UV—Monochromator 1 (240-850 nm)
6 Variable meas. diaphragm
7 Eyepiece
8 Scanning stage
9 Sample
10 Luminous field stop
11 Filter 1
12 Shutter
13 XBO lamp
14 Tungsten lamp
15 Shutter 2
16 Luminous field stop 2
17 Mirror 1

The instrument has a monochromator for incident illumination and excitation of the fluorochrome. The emission spectrum resulting from the excitation at various wavelengths can be resolved by a monochromator on the image side.

Small hair tresses of natural, unaltered dark brown European hair from DeMeo Brothers were "chemically damaged" by being subjected to sequential bleaching and perming. Conditioners were prepared containing the present invention and a "standard" Polyquaternium-7® in aqueous solution at concentrations between 0.25% and 0.5% active matter. These conditioner solutions were tagged with 0.1% of the fluorescent material.

In each case, 10-15 hair fibres were removed from each of the hair swatches and mounted in parallel on microscope slides. These fibres were considered as controls. The fibres were then reintroduced into the hair swatch, treated and rescanned after single and ten applications of the respective tagged conditioner solutions.

In each case, the excitation beam was projected onto the specimen mounted on a movable scanning stage. A variable measuring diaphragm controlled the size of the emission beam that enters the photometer, and its size and shape were determined by the available fluorescence intensity. Two different scanning modes were used for continuous measurements of fluorescence intensity along the fibre to provide detailed information on the distribution of the polymer on the hair and to record an average intensity profile along the length of the fibre.

Substantivity evaluation was carried out after one and ten applications of fluorescence-labelled conditioners containing the present invention and a "standard" Polyquaternium-7. Results for the present invention suggest that more of the conditioner-receptive acidic sites on the fibre surface were occupied and neutralised after a single application compared to a traditional Polyquaternium-7. This is shown in the appended Hair Substantivity bar graph.

Combing Force

Combing remains one of the most frequently used grooming methods and is an effort to arrange hair fibres in a parallel manner and frequently involves an initial detangling process. During combing the fibres are exposed to considerable frictional stresses, leading to surface damage and, in extreme cases, to split ends and hair breakage. Cationic conditioning polymers can provide lubrication to the hair and therefore reduce the inter-fibre forces and reduce hair damage.

The test was carried out using Instron Crosshead apparatus (shown in FIG. 2) described by Kamath Y K Weigmann H-D. J. Soc. Cosmet. Chem. 1986 37:111.

Figure 2:
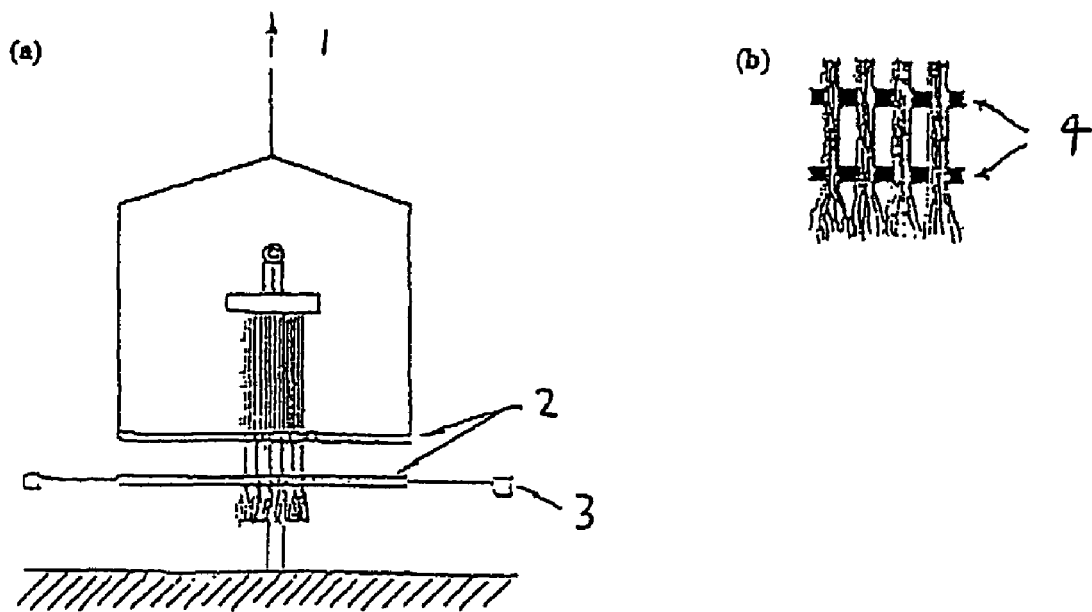
FIG. 2 is an illustration of an Instron Crosshead apparatus (double-comb modification).

In each case a comb is pulled through a hair tress and the forces of combing measured. The parameters used to describe the forces encountered when a comb passes through the hair are frequently referred to as the "midlength force" (ML) and "end-peak force" (EP). The midlength force is made up of inter-fibre friction and comb-fibre friction, whereas the end-peak force is attributable to tangle removal from the hair. The measurement of such forces is difficult to reproduce, and has led to the development of double-comb apparatus which is shown schematically in FIG. 2. In FIG. 2 the following key applies:
1 Load Cell
2 Combs
3 Instron Frame
4 Combs Testing was carried out on 18 cm long bleached and reduced tresses (for treatment details see above), treated with aqueous solutions of the present invention against a "standard" Polyquaternium-7® polymer. Combing force measurements, before and after conditioning, were made on an Instron tensile tester equipped with a double comb, and the mechanical resistance to combing was determined throughout the combing cycle. This is shown in the appended Combing Force bar graph.

Generally, polymeric conditioners have a tendency to increase the combing forces when they build up on the surface of the hair. In the case of the present invention, build up was very small and the negative effect on combing forces was not observed. On the contrary, the positive effect of cuticle reinforcement appeared to reduce inter-fibre friction and scale interlocking effects, which ultimately contribute to improvements in combing ease. The present invention again demonstrates an advantage over a "standard" Polyquaternium-7® polymer. This effect was observed at concentrations as low as 0.25% active polymer in a shampoo formulation.

Scale Lifting

Mechanical extension, such as combing and styling can lead to damage to the hair cuticle. This method is to evaluate the intactness of the cuticle sheath to determine the extent of damage and the protection against such damage offered by cationic conditioning polymers. A method has been developed by TRI, Princeton that measures intercuticular cohesion in the outermost cuticle layer. This method demonstrates scale-lifting phenomena that occur at characteristic extension levels resulting from stresses within the fibre caused by the extension.

Small hair strands (1 g) of natural unaltered dark brown European hair from DeMeo Brothers were used and exposed to 10 sequential applications with the respective formulations to study the cumulative effect of each product on the extension behaviour of the hair fibre. An appropriate number of hair fibres were removed after the first and tenth application for further studies.

The extension of the hair fibres was carried out on treated and untreated fibres which were mounted individually on a small metal frame and gradually extended at 50% RH at room temperature (22° C.). The hair fibre was observed as it extended under a fluorescence microscope with UV excitation. The extension levels at which certain levels of scale lifting occurred for each individual fibre were recorded, including hair fibre failure. The most common levels of scale lifting are:

B: the start of random scale lifting
C: scale edge lifting has become a common occurrence
D: extreme scale lifting in frequency and angle
E: hair fibre failure The hair fibres extended to failure were then used for scanning electron microscope investigation to determine what had occurred to the cuticula as the fibre broke. Overall scale lifting decreased after a single application and decreases even further after multiple treatments, demonstrating the great affinity that the cationic polymer has for the negatively charged sites of keratin. Scanning Electron Microscopy studies revealed that the conditioner of the present invention is strongly adsorbed onto the hair fibre surface even after one application, suggesting that most of the conditioner-receptive sites may be occupied and neutralised after a single conditioner application. In addition it was observed that shallow scale lifting occurring at the edge of the cuticle cell was preceded by frequent scale cracking. This modified scale lifting is believed to be conditioner induced and beneficial to hair, as it provides an alternate mechanism for stress release during extension of the hair fibre.

Results of these studies comparing the present invention to a "standard" Polyquaternium-7 demonstrate the advantages from the lower molecular weight material prepared as described above. This is shown in the 2 appended Scale Lifting Properties graphs.

Figure 3:
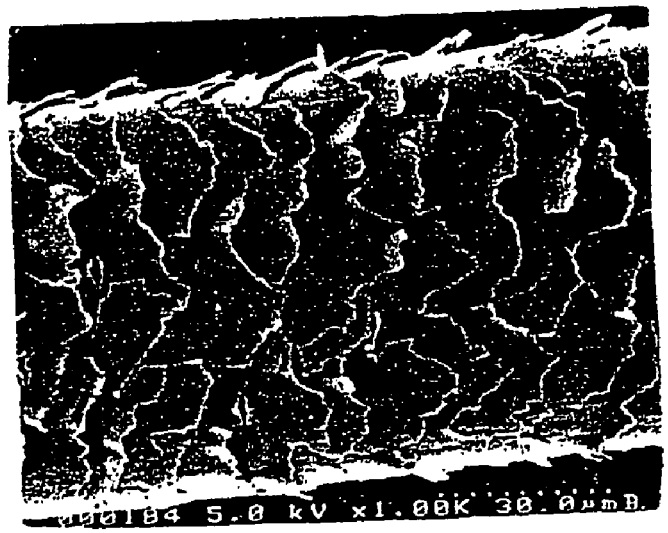
FIG. 3 is a an electromicrograph (SEM) of a hair sample treated with a composition containing Polyquaternium 7.
Figure 4:
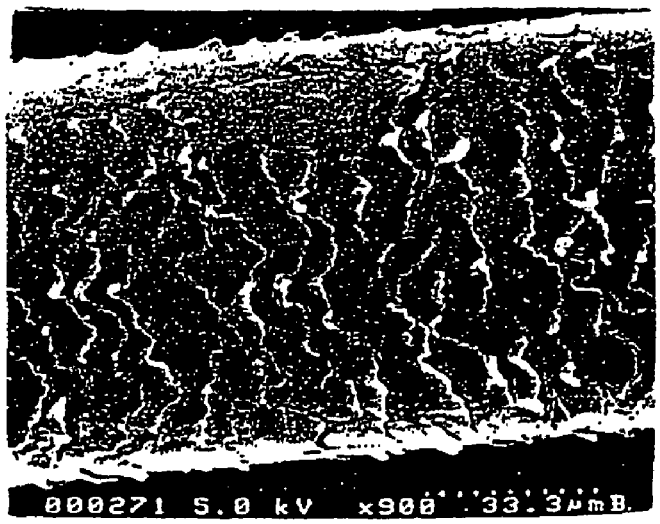
FIG. 4 is an electromicrograph (SEM) of a hair sample treated with a composition containing the cationic polymer according to the present invention.

An Scanning electromicrograph (SEM) of a hair sample treated with a composition containing the cationic polymer according to the present invention is shown in FIG. 4 and by comparison an SEM of a hair sample treated with a composition containing Polyquaternium 7 is shown in FIG. 3. It can clearly be seen that the present invention results in less scale lifting.

Half Head Studies

The formulation described below was prepared using the present invention and a "standard" Polyquaternium-7® polymer. These shampoos were used in half-head comparison studies using 20 volunteers with damaged hair over 3 weeks. The results are shown below:

Formulation for Consumer Study

| Ingredient | Amount |
| --- | --- |
| Deionised Water | To 100% |
| Conditioning Polymer (Present Invention/ "standard" Polyquaternium-7) | 0.25% active |
| Sodium Laureth Sulfate | 10% active |
| Cocamidopropyl Betaine | 1.5% active |
| Cocamide MEA | 2% active |
| Fragrance | 0.3% w/w |
| Sodium Chloride | 0.25% w/w |
| Phenonip | 0.5% w/w |
| Citric Acid | To pH 6 |

Testing Results

|  | Present Invention | Polyquaternium-7 |
| --- | --- | --- |
| Time to build foam during the pre-wash | 2.1 | 2.1 |
| Amount of foam during pre-wash | 2 | 2 |
| Amount of foam during main wash | 1 | 1 |
| Foam texture | 1.8 | 1.8 |
| Skin sensation | 1.7 | 1.7 |
| Rinseability | 2 | 2 |
| Wet combing | 2.1 | 2.7 |
| Wet grip | 1.9 | 2.7 |
| Drying properties | 2 | 2.3 |
| Drying time | 1.7 | 1.7 |
| Dry combing | 1.8 | 2.7 |
| Dry grip | 1.9 | 2.8 |
| Curl retention | 2.1 | 2 |
| Shine | 2.1 | 2.1 |
| Volume | 1.9 | 1.8 |
| Anti-static Effect | 1.1 | 1.3 |
| Manageability | 2.1 | 2 |
| Build-up effect | 1 | 1 |
| Build-up effect after 2 days | 2.2 | 2 |

1 = very good,
2 = good,
3 = satifactory,
4 = poor,
5 = very poor

The invention claimed is:

1. A method of preparing a detergent composition (formulation) for personal care, which comprises incorporating into said composition an aqueous solution of a cationic copolymer said solution containing less than 20 ppm residual monomer, wherein the cationic copolymer is formed from 20 to 30% by weight of cationic monomer and from 70 to 80% by weight of nonionic monomer selected from the group consisting of unsaturated N-substituted amides, (meth)acrylates having mono- or multi-hydroxy functional group(s) and acrylamide and derivatives thereof, wherein said cationic copolymer has an average molecular weight in the range 30,000 to 300,000 and the aqueous solution has a concentration of 20 to 50% by weight copolymer and a viscosity of from 1000 to 10,000 cP at 25° C.

2. A method according to claim 1 in which the cationic monomer is selected from the group consisting of diallyl dialkyl ammonium halides, dialkyl amino alkyl(meth)acrylamides, dialkyl amino alkyl(meth)acrylates, acid addition and quaternary ammonium salts thereof.

3. A method according to claim 1 in which the cationic monomer is a diallyl dialkyl ammonium halide.

4. A method according to claim 1 in which the cationic monomer is diallyl dimethyl ammonium chloride.

5. A method according to claim 1 in which the cationic monomer is diallyldimethyl ammonium chloride and the copolymer is 25 to 30% percent by weight of cationic monomer units.

6. A method according to claim 5 in which the nonionic monomer is acrylamide.

7. A method according to claim 1 in which the cationic copolymer has an average molecular weight of about 40,000 to about 150,000.

8. The method according to claim 1, wherein the detergent composition is a shampoo, skin cleanser, body wash formulation, or other detergent formulation used for personal hygiene.

* * * * *